US006212254B1

(12) United States Patent
Wilkins

(10) Patent No.: US 6,212,254 B1
(45) Date of Patent: *Apr. 3, 2001

(54) SIMPLIFIED CONDITIONS AND CONFIGURATIONS FOR PHASE-CONTRAST IMAGING WITH HARD X-RAYS

(76) Inventor: Stephen William Wilkins, 9 Halley Street, Blackburn, Victoria 3130 (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/430,491

(22) Filed: Oct. 29, 1999

Related U.S. Application Data

(63) Continuation of application No. 08/930,049, filed on Sep. 26, 1997, now Pat. No. 6,018,564.

(30) Foreign Application Priority Data

Mar. 28, 1995 (AU) ..................................... PN2012

(51) Int. Cl.⁷ .................................................. G21K 1/06
(52) U.S. Cl. ................................. 378/62; 378/82
(58) Field of Search ................... 378/62, 70, 82, 378/86, 87, 84

(56) References Cited

U.S. PATENT DOCUMENTS

| 4,953,188 | 8/1990 | Siegel et al. ............................ 378/48 |
| 5,173,928 | 12/1992 | Momose et al. ......................... 378/4 |
| 5,319,694 | 6/1994 | Ingal et al. ............................. 378/84 |
| 5,579,363 | 11/1996 | Ingal et al. ............................. 378/84 |
| 5,715,291 | 2/1998 | Momose .................................. 378/84 |
| 5,802,137 | 9/1998 | Wilkins .................................. 378/85 |
| 5,850,425 | 12/1998 | Wilkins .................................. 378/85 |
| 6,018,564 | * 1/2000 | Wilkins .................................. 378/62 |

FOREIGN PATENT DOCUMENTS 274155    7/1988    (EP) .

OTHER PUBLICATIONS

Davis, et al.; "Phase-contrast Imaging of weakly absorbing materials using hard X-rays"; Nature, vol. 373, Feb. 16, 1995, pp. 595–598.

* cited by examiner

Primary Examiner—David P. Porta
Assistant Examiner—Drew A. Dunn
(74) Attorney, Agent, or Firm—Fulwider Patton Lee & Utecht

(57) ABSTRACT

A method of obtaining an image of a boundary of an object, the boundary representing a refractive index variation, the method including irradiating the boundary with penetrating radiation having high lateral spatial coherence and a propagation component transverse to the refraction index variation, and receiving at least a portion of the radiation on an image plane so as to form the image, the radiation having been refracted by the boundary such that the boundary is represented on the image by a corresponding intensity variation. Additionally, the method may also include processing the image to resolve weaker variations.

35 Claims, 4 Drawing Sheets

0.1mm

SIMPLIFIED CONDITIONS AND CONFIGURATIONS FOR PHASE-CONTRAST IMAGING WITH HARD X-RAYS

CROSS-REFERENCES TO RELATED APPLICATIONS

Related Applications

This is a continuation of Ser. No. 08/930,049 filed Sep.26, 1997, now U.S. Pat. No. 6,018,564, and having an international filing date of Mar. 28, 1996.

BACKGROUND OF THE INVENTION

This invention relates generally to the observation of a structural feature of an object utilizing penetrating radiation such as x-rays. More particularly, but not exclusively, the invention relates to x-ray phase-contrast recordal, e.g. imaging, of internal boundary features.

The present applicant's international patent publication WO95/05725 (PCT/AU94/00480) and provisional patent application PN5811/95 disclose various configurations and conditions suitable for differential phase-contrast imaging using hard x-rays. Other disclosures are to be found in Soviet patent 1402871 and in U.S. Pat. No. 5,319,694. It is desired that relatively simpler conditions and configurations more closely related, at least in some embodiments, to traditional methods of absorption-contrast radiography, may be utilised for differential phase-contrast imaging with hard x-rays.

In accordance with the present invention there is provided a method of obtaining an image of a boundary of an object, said boundary representing a refractive index variation, said method including:

irradiating said boundary with penetrating radiation having high lateral spatial coherence and a propagation component transverse to said refraction index variation; and receiving at least a portion of said radiation on an image plane so as to form said image, said radiation having been refracted by said boundary such that said boundary is represented on said image by a corresponding intensity variation.

The present invention further provides an apparatus for obtaining an image of a boundary of an object, said boundary representing a refractive index variation, said apparatus including:

a source for irradiating said boundary with penetrating radiation having high lateral spatial coherence and a propagation component transverse to said refraction index variation; and a detector for receiving at least a portion of said radiation so as to form said image, said radiation having been refracted by said boundary such that said boundary is represented on said image by a corresponding intensity variation.

The present invention also provides a method of deriving a phase-contrast record of an internal boundary having a sharp refractive index variation or defined by a thickness variation, comprising:

irradiating the boundary with penetrating radiation having a propagation direction such that there is a significant component of the propagation vector transverse to the direction of said refractive index variation or in the direction of said thickness variation, and further having a lateral spatial coherence sufficiently high for the variation in refractive index or thickness to cause a detectable change in the local direction of propagation of the radiation wavefront at the boundary; and detecting and recording at least a portion of said radiation after it has traversed said boundary in a manner whereby an effect of said change in the local direction of propagation is observable and thereby recorded as a local diminution or rapid variation of intensity of the radiation which thereby substantially images the boundary.

The present invention further provides an apparatus for deriving a phase-contrast record of an internal boundary having a sharp refractive index variation or defined by a thickness variation, comprising:

means to irradiate the boundary with x-ray radiation having a propagation direction such that there is a significant component of the propagation vector transverse to the direction of said refractive index variation or in the direction of said thickness variation, and further having a lateral spatial coherence sufficiently high for the variation in refractive index or thickness to cause a detectable change in the local direction of propagation of the radiation wavefront at the boundary; and means to detect and record at least a portion of said radiation after it has traversed said boundary in a manner whereby an effect of said change in the local direction of propagation is observable and thereby recorded as a local diminution or rapid variation of intensity of the radiation which thereby substantially images the boundary.

The present invention also provides a method of obtaining an image of a boundary of an object, said boundary representing a refractive index variation, said method including:

irradiating said boundary with penetrating radiation having high lateral spatial coherence and a propagation component transverse to said refraction index variation; and receiving at least a portion of said radiation on an image plane so as to form said image, said radiation having been Fresnel diffracted by said boundary such that said boundary is represented on said image by a corresponding intensity variation.

The present invention further provides an apparatus for obtaining an image of a boundary of an object, said boundary representing a refractive index variation, said apparatus including:

a source for irradiating said boundary with penetrating radiation having high lateral spatial coherence and a propagation component transverse to said refraction index variation; and a detector for receiving at least a portion of said radiation so as to form said image, said radiation having been Fresnel diffracted by said boundary such that said boundary is represented on said image by a corresponding intensity variation.

The present invention also provides a method of determining the phase of an image, including processing phase-contrast image data of said image.

The intensity effect of a change in the local direction of propagation is preferably observable in an image comprising the record. The record and therefore the image may be photographic or electronic. The term "image" may thus refer, for example, to an observable effect in a set of intensity data, for example a table or other stored record of intensity values: the term is not confined to a visual context. The recording medium may comprise a two-dimensional pixilated detector, e.g. an electronic detector such as a charge-coupled device (CCD) array.

The irradiating means preferably includes a source of x-rays of diameter 20 micron or less, where diameter refers to the full width of intensity distribution of the source at half maximum intensity. The apparatus may advantageously further include a suitable stage or holder for samples containing the internal boundary being imaged.

The penetrating radiation, e.g. x-ray radiation, may be polychromatic and is preferably in the hard x-ray range, i.e. in the range 1 keV to 1 MeV.

The separation of the boundary and the detecting means is preferably selected to enhance the resolution of the image. For example, it has been observed that a sharper image, i.e. one with better contrast, is achieved by increasing separation. For instance contrast is improved at least for a separation of about 1 m relative to a separation of 0.4 m. This may partly be because background noise is diminished with increasing separation but the intensity variation effect arising from the change in the local direction of propagation is substantially preserved.

The term "lateral spatial coherence" herein refers to the correlation of the complex amplitudes of waves between different points transverse to the direction of propagation of the waves. Lateral spatial coherence is said to occur when each point on a wavefront has a direction of propagation which does not change over time. In practice, high lateral spatial coherence may, for example, be achieved by using a source of small effective size or by observing the beam at a large distance from the source. For example, for 20 keV x-rays a source size of 20 $\mu$m diameter or less would typically be appropriate. The smaller the source size the better for the purposes of this invention, provided total flux from the source is sufficient. Lateral spatial coherence may need to be preserved by careful selection of the x-ray window of the source, e.g. such that it is of highly uniform thickness and homogeneity.

SUMMARY OF THE INVENTION

Preferred embodiments of the present invention are hereinafter described, by way of example only, with reference to the accompanying Figures, in which.

DETAILED DESCRIPTION OF THE PREFERRED EMBODIMENTS

Figure 1:
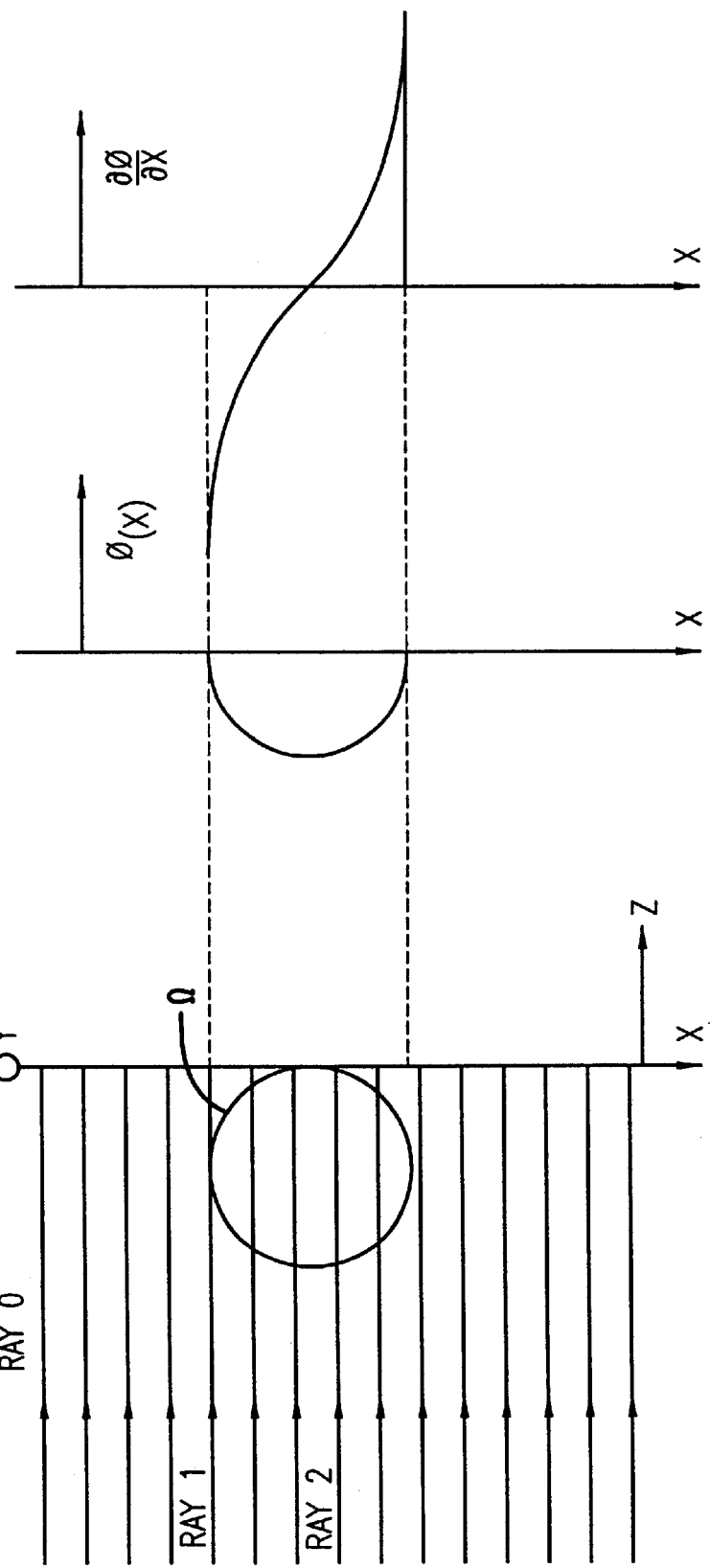
FIG. 1 is a diagram, presented in three parts for purposes of illustration, showing a circular cross-section object being irradiated by a parallel beam.

It is first now proposed to outline the mathematical basis of the present invention.

Variations in thickness and x-ray refractive index, $n(\lambda) = 1-\delta(\lambda)-i\beta(\lambda)$, of a sample will invariably lead to a change in the shape of an x-ray wavefront on passing through the sample. The real component $1-\delta(\lambda)$ of n relates to the degree of refraction and the imaginary component $-\beta(\lambda)$ relates to the degree of absorption. More specifically, for a single element substance $$\delta(\lambda) = \frac{r_o \lambda^2}{2\pi} N_o f_R \quad (1)$$

$$\beta(\lambda) = \frac{\lambda}{4\pi} \mu(\lambda) \quad (2)$$

where $\mu(\lambda)$ is the linear absorption coefficient, $r_o$ is the classical radius of an electron, $N_o$ is the number of atoms per unit volume and $f_R$ is the real part of the atomic scattering factor at zero scattering angle. The coefficient $\delta$ is proportional to $\lambda^2$ and $\beta$ is proportional to $\lambda^4$ and also $\lambda$ is proportional to 1/energy of the x-ray photon emitted from the source.

The magnitude of the wavefront distortions is related to the gradient of the phase variations transverse to the direction of propagation of the wavefront. In the geometrical optics approximation, the phase difference, $\phi$, for a ray path through an object is proportional to the integral of the decrement of the real part of the refractive index, $\delta$, along that ray path. For the coordinate system illustrated in FIG. 1 this can be expressed generally as $$\phi(x, z) = k \int_o^z \{n(x, z') - 1\} dz' \quad (3)$$

where k is equal to $2\pi/\lambda$. The angular deviation $\Delta\alpha$ of the local scattered wavevector from that of the local incident wavevector is proportional to the gradient of the phase difference in the direction perpendicular to the local incident wavevector. The word "local" refers to a point (x,y,z) on the wavefront. Mathematically the local scattered wavevector can be written for the coordinate system illustrated in FIG. 1 as $$s(x, y, z) \simeq \left(\frac{\partial \phi}{\partial x}, \frac{\partial \phi}{\partial y}, k\right) \quad (4)$$

where s(x,y,z) is the normal to the wavefront at point (x,y,z) and the above relationship is valid in the paraxial approximation when $(\partial\phi/\partial x)^2 + (\partial\phi/\partial y)^2 \ll k^2$. The angular deviation $\Delta\alpha$ can be expressed as $$\Delta\alpha \simeq \frac{1}{k}\frac{\partial \phi(x, z)}{\partial x} = \int_o^z \left\{\frac{\partial n(x, z')}{\partial x} - 1\right\} dz'. \quad (5)$$

The angular deviation $\Delta\alpha$ is therefore dependent on a refractive index variation perpendicular to a propagation wavevector, and the amount of deviation depends on the length over which the variation occurs in the direction of the wavevector, e.g. the thickness of a sample.

Figure 2:
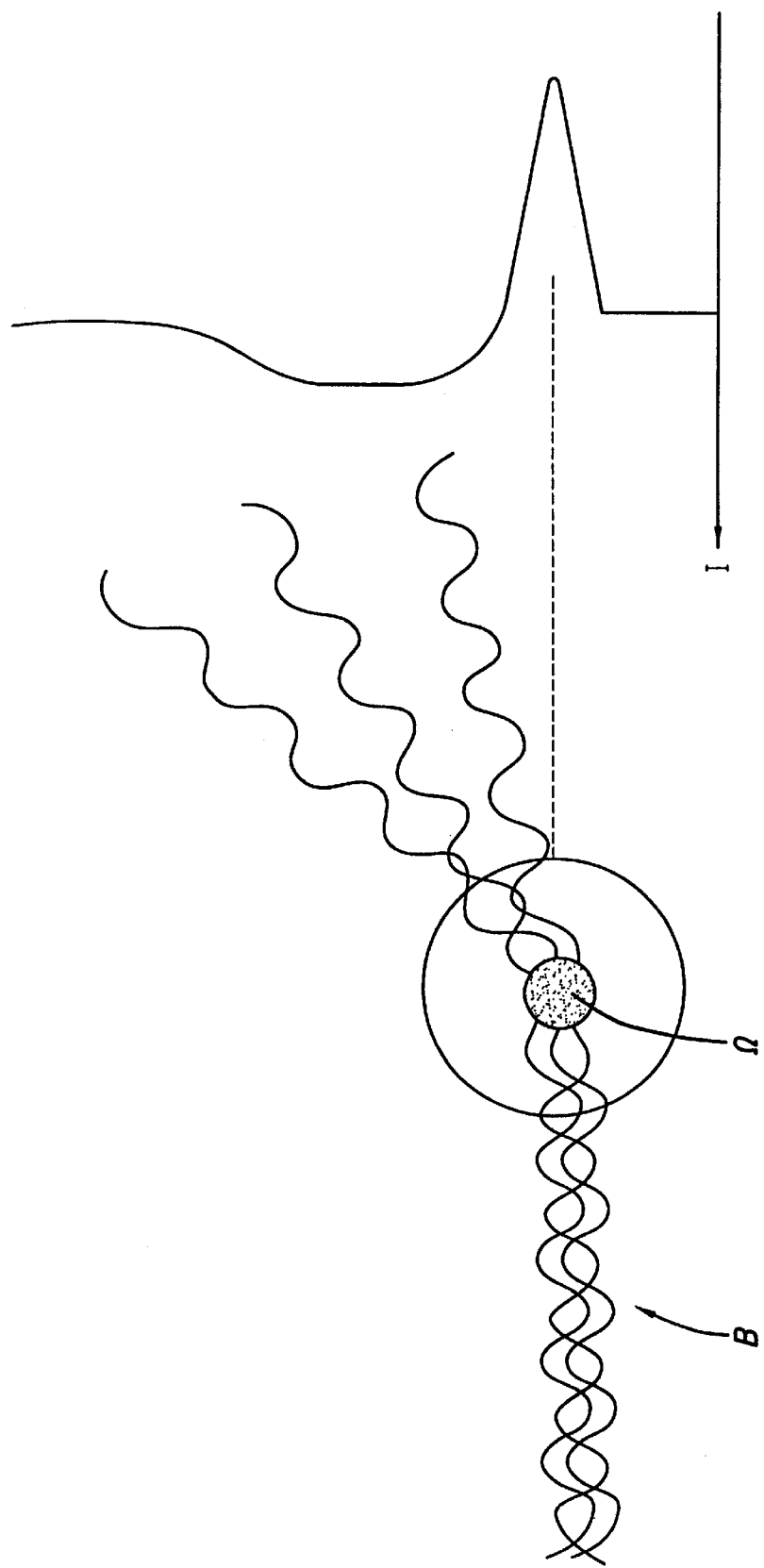
FIG. 2 is a diagram of a circular cross-section object being irradiated by a polychromatic beam and the intensity of the phase-contrast image produced.

To illustrate the nature of the effect, consider the case of a spherical object, $\Omega$, of refractive index $n_M$ embedded in a medium of refractive index $n_o=1$, as illustrated in FIGS. 1 and 2.

The x-ray optical path length differences through the sample relative to through a vacuum lead to a phase difference $\phi(x)$ and hence to a phase gradient $\partial\phi/\partial x$ in the direction (FIG. 1) transverse to the local direction of propagation. The phase difference between ray 1 which passes through the object $\Omega$ parallel to the z-axis at constant distance from it and the reference ray 0 is:

$$\phi(x, y) = \frac{2\pi}{\lambda} \int_{-z(x,y)}^{0} \delta(\lambda) dt = \frac{2\pi}{\lambda} \delta(\lambda) x(x, y), \qquad (6)$$

where z(x,y) is the length of the intersection of ray 1 with $\Omega$ and $$z(x,y) = 2\sqrt{R^2 - x^2 - y^2}, \qquad (7)$$

and R is the radius of $\Omega$ and $\delta$ is the decrement of refractive index coefficient. Mathematically, for a circular sectioned object in the x-z plane, the expression for $\partial \phi / \partial x$ and the angular deviation ha between an incident ray and the corresponding refractive ray for a given x is:

$$\begin{aligned} \Delta \alpha &= \frac{1}{k} s(x, y, z) \\ &= \frac{\lambda}{2\pi} \frac{\partial \phi}{\partial x} \\ &= -2\delta(\lambda) \left[ \frac{x}{\sqrt{R^2 - x^2}} \right]. \end{aligned} \qquad (8)$$

In equation (8), $\delta(\lambda)$ is slowly varying and it can readily be seen that the phase gradient diverges at $x = \pm R$, where the rays can deviate by very large angles from the optic axis. In these limits, the angular deviations of the scattered beams can be very large and lead to an observable loss in intensity I in the corresponding forward direction, the position of which is independent of wavelength, as shown in FIG. 2 for a polychromatic beam B. The decrement of refractive index coefficient, $\delta$, is typically of order $10^{-5}$ to $10^{-6}$ for light elements and hard x-rays but nevertheless the deviation angle $\Delta \alpha$ may be quite large when x is close to $\pm R$, i.e. at the boundary of the sample or at an internal boundary feature.

The nature of the contrast obtained under different conditions of source size, object-source distance and object-image distance, and also the spectral distribution of the source need to be considered. A further consideration affecting contrast is the degree of modification of the wavefront introduced by the object.

For the plane-wave case, to help understand the role of these factors on contrast in image formation, we can to a first approximation use the formula derived by Cowley (J. M. Cowley, "Diffraction Physics", 2nd Ed., p.60, North Holland, 1981) for the Fresnel diffraction contrast from a phase object. According to this formal, for a one-dimensional phase object producing a phase change, $\phi(x)$, under plane-wave illumination with wavelength $\lambda$, the intensity distribution at a distance $R_2$ from the object is given by $$I(x) = 1 + \frac{R_2 \lambda}{2\pi} \phi''(x) \qquad (9)$$

which is valid to first order in the quantity $(R_2 \lambda / 2\pi) \phi''(x)$, assumed small. From this apparently simple formula, one can draw some significant conclusions, namely:

i) the contrast varies directly with $R_2$,
ii) the structure of the image is $\lambda$-independent. Only the contrast is affected. For a polychromatic source one would simply replace $\lambda$ in the formula by a spectrally weighted sum.

To get some feeling for the range of validity of the above formula for the present x-ray case, let us suppose there is an object feature for which the phase transmitted by the object varies by 1 radian over a lateral distance of 10 microns. Then $\phi'' \sim 10^{10} m^{-2}$, and for $\lambda \sim 1$ Å, $R_2 \sim 1$m, we see that $(R_2 \lambda / 2\pi) \phi''(x) \leq 1$. Thus the formula should be valid even for small phase objects or reasonably rapid variations in phase. However, for very sharp edges or changes of slope, such as are often used in calculations of artificial test objects (e.g. fibres), $\phi''$ may become too large (even infinite), so the formula breaks down. But even in these cases the general form of the image (a black/white line from a sharp step object) is reproduced but not the subsidiary fringes typical of diffraction from such discontinuities. On the other hand, and probably of more practical significance, we see that for smaller $\phi''(x)$, i.e. larger features with less rapid lateral variation, the contrast will be low, and may well limit the practical visibility.

A more exact mathematical treatment of this type of imaging with plane-waves has recently been carried out in terms of Fresnel diffraction (P. Cloetens, R. Barrett, J. Baruchel, J. P. Guigay and M. Schlenker, J. Phys. D.: Appld. Phys., 1996 29, 133–46; J. P. Guigay, Optik, 1977 49, 121–5). Their treatment gives the same equation as presented above to first order. However the more accurate treatment leads to the conclusion that the maximum contrast for a spatial frequency u occurs when $2 \lambda R_2 u^2 = 1$, at least for the normal range of conditions expected in phase-contrast radiography. The spatial frequency u relates to the structure of the object being imaged, where u equals 1/A where A is the spatial period of a Fourier component of the imaged object.

These treatments all refer to illumination with an ideal plane-wave. Any divergence in the beam will blur the image by an amount proportional to $R_2$ (in this respect behaving in the same way as in conventional radiography). The above authors (Cloetens et al.) then show that the overall optimum $R_2$, taking into account both contrast and resolution is given by $$R_2 \leq 2\lambda / \alpha^2 \qquad (10)$$

where $\alpha = s / R_1$ is the angle subtended by the source at the object and relates to the (almost) plane-wave case. It should be noted that Cloetens et al. specifically prescribe the need for a highly monochromatic source of x-rays and consider only the plane-wave case in contradistinction to the preferred embodiments described herein.

As pointed out, the treatments above relate specifically to the plane-wave case whereas we are principally concerned with the spherical-wave case which more closely relates to convention radiography. To help understand the spatial-wave case, we now consider the relationship between the two which can be usefully established via a simple analysis of the Fresnel-Kirchhoff expression for imaging an object with a point source at a distance $R_1$ from the object (the spherical-wave case). This shows that there is a simple relationship for the spherical-wave case involving terms of the plane-wave case but with a modified object to image distance R', such that $$\frac{1}{R'} = \frac{1}{R_1} + \frac{1}{R_2} \qquad (11)$$

and with the image magnified by $(R_1 + R_2) / R_1$. From simple geometrical arguments, based on ray optics, it appears that loss of contrast or resolution due to source size will not be a problem in the spherical-wave case as both the image and the source size are magnified, the latter by $R_2 / R_1$ which asymptote to the same factor for large $R_2$. The factor affecting contrast for the spherical-wave case is that (for the range of energies and spatial resolutions relevant for radiography) $2\lambda R_2(1+R_2/R_1)u^2$ should be large (but is typically less than 1). This expression may be large because $R_2$ is large, or $\lambda$ large or the spatial frequency, u, is large. As an illustration, for practical radiographic purposes the following values might serve as being indicative $\lambda=0.2$ Å; $u \leq 2 \times 10^5$ (corresponding to a spatial period of 20 micron or more) so that $R_2 \approx 2.5$ m (assuming $R_2/R_1=3$, say) would give maximum contrast for the highest spatial frequency. Larger values of $R_2$ would be appropriate for maximum contrast of lower spatial frequencies.

It may be noted that the function $\phi''$ will tend to enhance the edges and boundaries of a phase object in an image. If there is also an absorptive component of the object it will, at least to first order, add directly to the image contrast (e.g. see Equation 7 in Guigay, 1977). The present technique could complement and enhance the usual radiological image, as well as yielding new information. It may also be noted that proper treatment of the contrast in an image involving differential phase-contrast (involving the Laplacian of $\phi$) requires numerical processing of the image via, for example, solution of the transport of intensity equations (see T. E. Gureyev, A. Roberts and K. Nugent, Journal of Optical Society of America, Vol. A12, pp.1932 and pp.1942, 1995 incorporated herein by reference) in order to retrieve the phase, $\phi(x)$.

Figure 3:
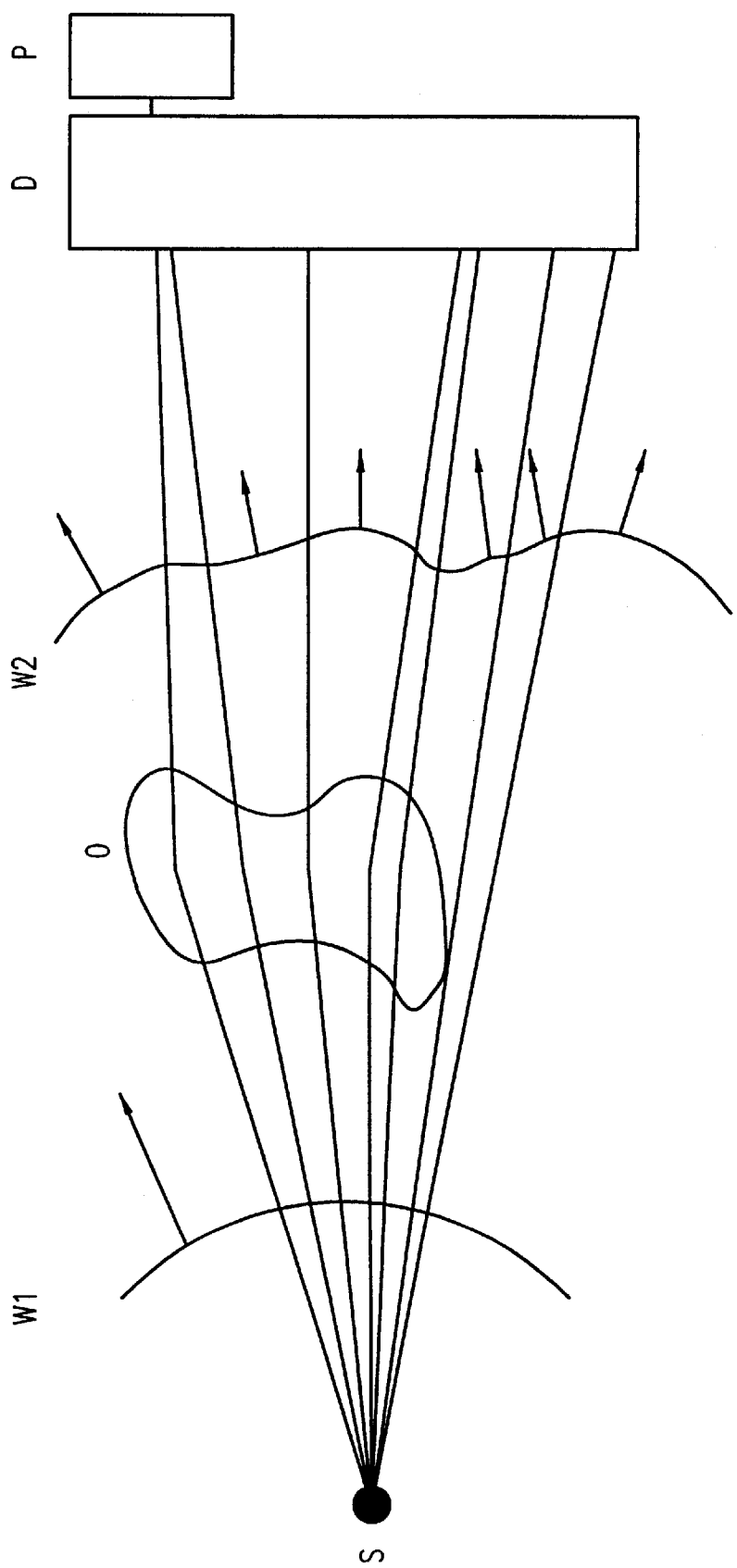
FIG. 3 is a diagram of an x-ray optics configuration according to an embodiment of the invention.

We turn now to practical arrangements for applying the concept arising from these determinations. In a first embodiment (FIG. 3), there is a source S of high spatial coherence and an x-ray imaging detector D, for example film, photostimulable phosphor plates (e.g. Fuji Image Plates), or a two-dimensional electronic detector, for recording images for processing P utilizing the formulae and techniques discussed above. Regions of sharp refractive index variation transverse to the direction of propagation, or thickness variation in the direction of propagation, can lead to a significant change in the local direction of propagation of the wavefront passing through those regions. Thus a spherical wavefront W1 emanating from the point source S, which may be considered to be unfocused, becomes distorted to W2 on passing through the object O. This distorted, unfocused wavefront falls upon and is detected by x-ray detector D. By recording the intensity of the wavefront at a sufficient distance from the sample, intensity variations due to sharp refractive index and thickness variations in the sample may be detected and their location recorded in an image. This corresponds to a form of differential phase-contrast imaging. The location of the imaging detector is chosen such that the spatial resolution of the detector is sufficient to resolve the intensity differences arising from the severe distortions of the wavefront and to optimise contrast, as described above, subject to practical considerations.

Typically, the sharp gradients in refractive index or thickness will be imaged as sharp losses or rapid variation in intensity at corresponding points in the image. This feature of intensity loss or rapid variation at a given point in the image is essentially independent of wavelength and can therefore lead to very sharp contrast variations in the image even when a polychromatic source is used.

This configuration has the feature that for a circular source distribution, the spatial resolution in the image is the same for both directions and is essentially determined by the source size. It also has the advantage that considerable magnification of the image is possible and so recording media such as Fuji Image Plates may be used which have many desirable properties such as wide dynamic range and high sensitivity but not high spatial resolution.

In addition to the source and detector involved in this configuration, a high resolution angular analyzer may be inserted between the sample and the detector. The high resolution angular analyser might for example be a suitably curved crystal in Laue geometry with curvature chosen for some appropriate characteristic wavelength of the source. This variation in the method is aimed at resolving weaker variations in refractive index and thickness of the sample than are observable with the first described configuration.

It may be noted that a very substantial magnification of the image is possible so that very high spatial resolution in the image may be achieved even with much lower spatial resolution detectors such as Fuji Image Plates. Also it may be noted that since the method of image formation is essentially independent of x-ray energy, the sources can be operated at high tube voltage and so lead to lower absorbed dose to the sample, which is important in clinical applications.

Figure 4:
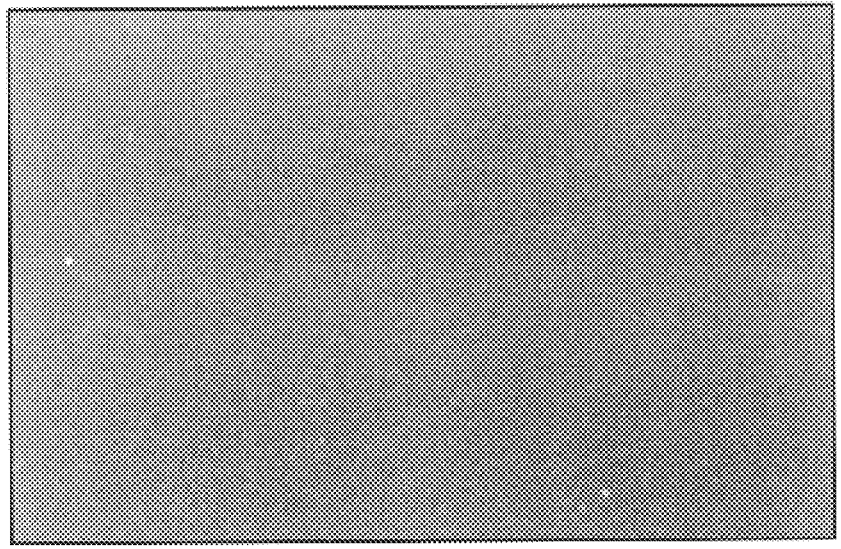
FIGS. 4 and 5 are x-ray images of various boundaries derived in accordance with the invention, as subsequently detailed herein.
Figure 5:
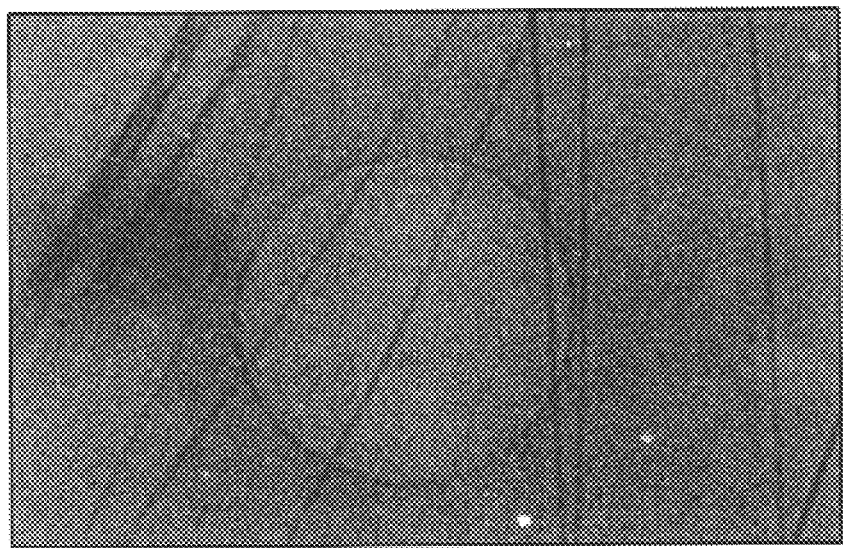

Some examples of phase-contrast images recorded using the aforementioned technique are illustrated in FIGS. 4 and 5. FIG. 4 shows an image of the edge of a 10 $\mu$m plastic film which is the same as that used in Davis, Gao, Gureyev, Stevenson and Wilkins (Phys. Rev. Letters, 1995, Vol. 74, p. 3173) and corresponds to a pure phase object. FIG. 5 shows images of an air bubble and glass fibres in a polymer matrix based on a similar sample to that reported in Davis, Gao, Gureyev, Stevenson and Wilkins (Nature Vol. 373 pp. 595–8, 1995) and corresponds to an almost pure phase object. In each case clear additional contrast can be seen over that expected for a normal absorption-contrast image. In particular, in FIG. 4 the edge of the film is clearly visible as a black/white contrast feature as also are the edges of the bubbles and the fibres. The source used was a nominal 10 $\mu$m diameter microfocus source (Kevex Model PXS) with Cu anode operated at 40 kV. For FIG. 4 the source to sample and sample to film distances were both 700 mm while for FIG. 5 the corresponding distances were 120 mm and 1000 mm, respectively. It should be noted that contrast in the present instances is visible almost entirely due to the high spatial coherence of the source. The contrast is primarily an intensity loss contrast and in that sense resembles normal absorption but is different in that it represents an intensity loss due to refractive scattering (or Fresnel diffraction) at the object boundaries as shown by equation (8). A normal fine focus source of diameter 0.1 mm would have a projected size of approximately the length of the 0.1 mm scale bar shown on the photographs and so largely smear out this contrast.

To provide a comparison of phase-contrast imaging as described herein and standard absorption imaging, the table below sets out the absorption thickness $t_a$ of a carbon sample required to achieve 65% absorption and the phase thickness $t_p$ of the sample required to achieve a phase change in $\phi$ of $2\pi$, for different source energies E.

TABLE 1

| E keV | $\lambda$(Å) | $t_a(\mu m)$ | $t_p(\mu m)$ |
|---|---|---|---|
| 50 | 0.25 | 435000 | 133 |
| 12 | 1 | 5000 | 30 |
| 1.2 | 10 | 4 | 3 |
| 0.25 | 50 | 1.3 | 1.2 |

The results in the table illustrate how phase-contrast imaging can be used to image very small objects with high energy sources.

Advantageously, the beam path between sample and detector may involve evacuated tubes with x-ray transparent windows or similar means to reduce the effects of air scattering making sure that their optical quality is such that they do not have a detrimental effect on the coherence of the x-ray beam.

The present method should be especially well suited to imaging of such features as cracks, voids and delamination effects in various types of materials, since these features involve maximum differences in x-ray refractive index and the spatial variation can be extremely sharp. To give observable contrast, the source is preferably of a very small effective size, say less than of order 20 µm, and the detector is preferably a high resolution imaging detector such as x-ray film or a two-dimensional electronic detector, e.g. a CCD array. The method may also prove useful in significantly enhancing the contrast of important features in clinical radiography.

The present application outlines some simplified conditions and configurations for differential phase-contrast imaging using penetrating radiation such as hard x-rays, which are particularly aimed at clinical and industrial applications. These new approaches are more closely related to traditional methods used for absorption-contrast radiography and should be easier to implement than our earlier described methods of the aforementioned WO95/05725 and PN5811/95, especially for large areas of irradiation. They should also have considerably shorter exposure times for a given source power than the earlier monochromatic methods since they may use a very wide spectrum from the source.

Throughout this specification, unless the context requires otherwise, the word "comprise", or variations such as "comprises" or "comprising", will be understood to imply the inclusion of a stated integer or group of integers but not the exclusion of any other integer or group of integers.

What is claimed is:

1. A method of obtaining an image of a boundary of an object, said boundary representing a refractive index variation, said method comprising:
   irradiating said boundary with a propagated wavefront of x-rays having high lateral spatial coherence and a propagation component transverse to said refractive index variation;
   detecting intensity of at least a portion of said wavefront of said x-rays passing through said boundary so as to form said image, said x-rays having been refracted by said boundary such that said boundary is represented on said image by a corresponding variation in the detected intensity of said wavefront in said image; and
   processing said image so as to derive from the image said corresponding variation in the detected intensity of said wavefront in said image and so identify the representation of the boundary.

2. A method as claimed in claim 1, wherein said x-rays are polychromatic.

3. A method as claimed in claim 1, wherein said step of irradiating said boundary comprises irradiating said boundary with an unfocused propagated wavefront of x-rays, and wherein said step of detecting intensity comprises detecting intensity of at least a portion of said wavefront of said x-rays passing through said boundary so as to form said image without focusing said wavefront after it passes through said boundary.

4. A method as claimed in claim 1, including separating the boundary and the position of detecting said intensity of at least a portion of said wavefront by a distance sufficient to enhance the contrast of said variation in the detected intensity of said wavefront.

5. A method as claimed in claim 4, wherein said distance is greater than or equal to 0.3 m.

6. A method as claimed in claim 5, wherein said distance is greater than or equal to 0.7 m.

7. A method as claimed in claim 1, wherein said x-rays have an energy in the range 1 keV to 1 MeV.

8. A method as claimed in claim 1, including generating said x-rays with a source less than or equal to 20 µm in diameter.

9. A method as claimed in claim 1, wherein said variation in the detected intensity of said wavefront is sharp and localized.

10. An apparatus for obtaining an image of a boundary of an object, said boundary representing a refractive index variation, said apparatus comprising:
    a source for irradiating said boundary with a propagated wavefront of x-rays having high lateral spatial coherence and a propagation component transverse to said refractive index variation;
    a detector for detecting intensity of at least a portion of said wavefront of said x-rays so as to form said image, said x-rays having been refracted by said boundary such that said boundary is represented on said image by a corresponding variation in the detected intensity of said wavefront in said image; and
    means for processing said image so as to derive from the image said corresponding variation in the detected intensity of said wavefront in said image and so identify the representation of the boundary.

11. An apparatus as claimed in claim 10, further including holder means to hold an object containing said boundary and so locate the boundary at a predetermined position, whereby a separation distance between said boundary and said detector may be set to enhance the contrast of said variation in the detected intensity of said wavefront.

12. An apparatus as claimed in claim 11, wherein said detector and said holder means are disposed so that said distance is greater than or equal to 0.3 m.

13. An apparatus as claimed in claim 11, wherein said detector and said holder means are disposed so that said distance is greater than or equal to 0.7 m.

14. An apparatus as claimed in claim 10, wherein said source generates x-rays with energy in the range 1 keV to 1 MeV.

15. An apparatus as claimed in claim 10, wherein said source has a diameter less than or equal to 20 µm.

16. An apparatus as claimed in claim 10, wherein said x-rays are polychromatic.

17. An apparatus as claimed in claim 10, wherein said variation in the detected intensity of said wavefront is sharp and localized.

18. A method of deriving a phase-contrast record of an internal boundary representing a sharp refractive index variation comprising:
    irradiating the boundary with a propagated wavefront of x-rays having a propagation direction such that there is a significant component of the propagation vector transverse to the direction of said refractive index variation, and further having a lateral spatial coherence sufficiently high for the variation in refractive index to cause a detectable change in the local direction of propagation of the wavefront of x-rays at the boundary;
    detecting and recording intensity of at least a portion of said wavefront of x-rays after it has traversed said boundary in a manner whereby an effect of said change in the local direction of propagation is observable to form a record of a local diminution or rapid variation of intensity of the x-rays which thereby substantially detects the boundary; and processing said record so as to derive from the record said corresponding variation in the detected intensity of said wavefront in said record and so identify the representation of the boundary.

19. A method as claimed in claim 18, wherein said x-rays are polychromatic.

20. A method as claimed in claim 18, wherein said step of irradiating said boundary comprises irradiating said boundary with an unfocused propagated wavefront of x-rays, and wherein said step of detecting intensity comprises detecting intensity of at least a portion of said wavefront of said x-rays passing through said boundary so as to form said record without focusing said wavefront after it passes through said boundary.

21. A method as claimed in claim 18, including separating said boundary and the position of detecting said portion of said x-rays by a distance which enhances the contrast and/or resolution of the part of an image comprising the record of said local diminution or rapid variation of wavefront intensity.

22. A method as claimed in claim 18, wherein said x-rays have an energy in the range 1 keV to 1 MeV.

23. A method as claimed in claim 18, wherein said step of irradiating comprises irradiating said boundary with an x-ray source having a diameter less than or equal to 20 µm.

24. A method as claimed in claim 21, wherein said distance is greater than or equal to 0.3 m.

25. A method as claimed in claim 21, wherein said distance is greater than or equal to 0.7 m.

26. An apparatus for deriving a phase-contrast record of an internal boundary representing a sharp refractive index variation, comprising:
  means to irradiate the boundary with a propagated wavefront of x-rays having a propagation direction such that there is a significant component of the propagation vector transverse to the direction of said refractive index variation, and further having a lateral spatial coherence sufficiently high for the variation in refractive index to cause a detectable change in the local direction of propagation of the wavefront of x-rays at the boundary; and
  means for detecting and recording intensity of at least a portion of said wavefront of x-rays after it has traversed said boundary in a manner, whereby an effect of said change in the local direction of propagation is observable to form a record of a local diminution or rapid variation of intensity of the wavefront of x-rays which thereby substantially detects the boundary; and
  means for processing said record so as to derive from the record said corresponding variation in the detected intensity of said wavefront in said record and so identify the representation of the boundary.

27. An apparatus as claimed in claim 26, wherein said x-rays are polychromatic.

28. An apparatus as claimed in claim 26, wherein said x-rays have an energy in the range 1 keV to 1 MeV.

29. An apparatus as claimed in claim 26, wherein said means to irradiate is a source less than or equal to 20 µm in diameter.

30. An apparatus as claimed in claim 26, further including holder means to hold an object containing said boundary and so locate the boundary at a predetermined position, whereby the separation of said boundary and the position of detecting said portion of said wavefront of x-rays may be set at a distance which enhances the contrast and/or resolution for part of an image comprising the record of said local diminution or rapid wavefront variation of intensity.

31. An apparatus as claimed in claim 30, wherein said detection means and said holder means are disposed so that said distance is greater than or equal to 0.3 m.

32. An apparatus as claimed in claim 30, wherein said detection means and said holder means are disposed so that said distance is greater than or equal to 0.7 m.

33. A method of obtaining an image of a boundary of an object, said boundary representing a refractive index variation, said method comprising:
  irradiating said boundary with a propagated wavefront of x-rays having high lateral spatial coherence and a propagation component transverse to said refractive index variation;
  detecting intensity of at least a portion of said wavefront of said x-rays so as to form said image, said x-rays having been Fresnel diffracted by said boundary such that said boundary is represented on said image by a corresponding variation in the detected intensity of said wavefront in said image; and
  processing said image so as to derive from the image said corresponding variation in the detected intensity of said wavefront in said image and so identify the representation of the boundary.

34. A method as claimed in claim 33, wherein said step of irradiating said boundary comprises irradiating said boundary with an unfocused propagated wavefront of x-rays, and wherein said step of detecting intensity comprises detecting intensity of at least a portion of said wavefront of said x-rays passing through said boundary so as to form said image without focusing said wavefront after it passes through said boundary.

35. An apparatus for obtaining an image of a boundary of a object, said boundary representing a refractive index variation, said apparatus comprising:
  a source for irradiating said boundary with a wavefront of x-rays having high lateral spatial coherence and a propagation component transverse to said refractive index variation; and
  a detector for receiving at least a portion of said wavefront of said x-rays passing through said boundary so as to form said image, said x-rays having been Fresnel diffracted by said boundary such that said boundary is represented on said image by a corresponding variation in the detected intensity of said wavefront in said image; and
  means for processing said image so as to derive from the image said corresponding variation in the detected intensity of said wavefront in said image and so identify the representation of the boundary.

* * * * *

(12) EX PARTE REEXAMINATION CERTIFICATE (6211th)
United States Patent
Wilkins

(10) Number: US 6,212,254 C1
(45) Certificate Issued: *Apr. 29, 2008

(54) SIMPLIFIED CONDITIONS AND CONFIGURATIONS FOR PHASE-CONTRAST IMAGING WITH HARD X-RAYS

(75) Inventor: Stephen William Wilkins, Blackburn (AU)

(73) Assignee: X-ray Technologies Pty Ltd., Melbourne, Victoria (AU)

Reexamination Request:
No. 90/007,530, Apr. 29, 2005

Reexamination Certificate for:
Patent No.: 6,212,254
Issued: Apr. 3, 2001
Appl. No.: 09/430,491
Filed: Oct. 29, 1999

(*) Notice: This patent is subject to a terminal disclaimer.

Related U.S. Application Data

(63) Continuation of application No. 08/930,049, filed on Sep. 26, 1997, now Pat. No. 6,018,564.

(30) Foreign Application Priority Data

Mar. 28, 1995 (AU) .............................................. PN2012

(51) Int. Cl.
*G21K 1/06* (2006.01)

(52) U.S. Cl. .......................................... 378/62; 378/82

(58) Field of Classification Search ....................... None
See application file for complete search history.

(56) References Cited

U.S. PATENT DOCUMENTS 5,187,726 A * 2/1993 White .......................... 378/35

FOREIGN PATENT DOCUMENTS

JP A-4-265808 9/1992

OTHER PUBLICATIONS

V. White and F. Cerrina, Metal–less X–Ray Phase Shift Masks for Nanolithography, Journal of Vacuum Science & Technology, B 10(6), Nov./Dec. 1992, pp. 3141–3144.

* cited by examiner

*Primary Examiner*—Margaret Rubin

(57) ABSTRACT

A method of obtaining an image of a boundary of an object, the boundary representing a refractive index variation, the method including irradiating the boundary with penetrating radiation having high lateral spatial coherence and a propagation component transverse to the refraction index variation, and receiving at least a portion of the radiation on an image plane so as to form the image, the radiation having been refracted by the boundary such that the boundary is represented on the image by a corresponding intensity variation. Additionally, the method may also include processing the image to resolve weaker variations.

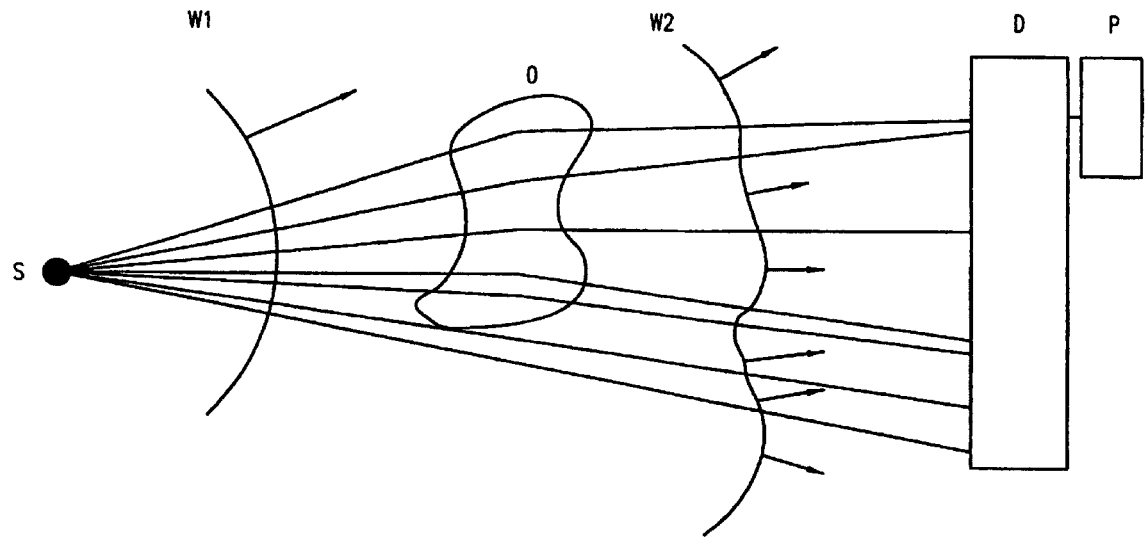

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 18–32 is confirmed.

Claims 1, 10, 33 and 35 are determined to be patentable as amended.

Claims 2–9, 11–17 and 34, dependent on an amended claim, are determined to be patentable.

New claims 36–47 are added and determined to be patentable.

1. A method of obtaining an image of a boundary [of] *within* an object, said boundary representing a refractive index variation, said method comprising:
   irradiating said boundary with a propagated wavefront of x-rays having high lateral spatial coherence and a propagation component transverse to said refractive index variation;
   detecting intensity of at least a portion of said wavefront of said x-rays passing through said boundary so as to form said image, said x-rays having been refracted by said boundary such that said boundary is represented on said image by a corresponding variation in the detected intensity of said wavefront in said image; and
   processing said image so as to derive from the image said corresponding variation in the detected intensity of said wavefront in said image and so identify the representation of the boundary.

10. An apparatus for obtaining an image of a boundary [of] *within* an object, said boundary representing a refractive index variation, said apparatus comprising:
   a source for irradiating said boundary with a propagated wavefront of x-rays having high lateral spatial coherence and a propagation component transverse to said refractive index variation;
   a detector for detecting intensity of at least a portion of said wavefront of said x-rays so as to form said image, said x-rays having been refracted by said boundary such that said boundary is represented on said image by a corresponding variation in the detected intensity of said wavefront in said image; and
   means for processing said image so as to derive from the image said corresponding variation in the detected intensity of said wavefront in said image and so identify the representation of the boundary.

33. A method of obtaining an image of a boundary [of] *within* an object, said boundary representing a refractive index variation, said method comprising:
   irradiating said boundary with a propagated wavefront of x-rays having high lateral spatial coherence and a propagation component transverse to said refractive index variation;
   detecting intensity of at least a portion of said wavefront of said x-rays so as to form said image, said x-rays having been Fresnel diffracted by said boundary such that said boundary is represented on said image by a corresponding variation in the detected intensity of said wavefront in said image; and
   processing said image so as to derive from the image said corresponding variation in the detected intensity of said wavefront in said image and so identify the representation of the boundary.

35. An apparatus for obtaining an image of a boundary [of] *within* a object, said boundary representing a refractive index variation, said apparatus comprising:
   a source for irradiating said boundary with a wavefront of x-rays having high lateral spatial coherence and a propagation component transverse to said refractive index variation; and
   a detector for receiving at least a portion of said wavefront of said x-rays passing through said boundary so as to form said image, said x-rays having been Fresnel diffracted by said boundary such that said boundary is represented on said image by a corresponding variation in the detected intensity of said wavefront in said image; and
   means for processing said image so as to derive from the image said corresponding variation in the detected intensity of said wavefront in said image and so identify the representation of the boundary.

*36. A method as claimed in claim 1, wherein said x-rays penetrate the object to irradiate the boundary, and said portion of the wavefront of the x-rays is detected after it has traversed the boundary and emerged from the object.*

*37. Apparatus as claimed in claim 10, wherein said source generates x-rays that penetrate the object to irradiate the boundary, and said detector is positioned for detecting said portion of the wavefront of the x-rays after it has traversed the boundary and emerged from the object.*

*38. A method as claimed in claim 33, wherein said x-rays penetrate the object to irradiate the boundary, and said portion of the wavefront of the x-rays is detected after it has traversed the boundary and emerged from the object.*

*39. Apparatus as claimed in claim 35, wherein said source generates x-rays that penetrate the object to irradiate the boundary, and said detector is positioned for detecting said portion of the wavefront of x-rays after it has traversed the boundary and emerged from the object.*

*40. A method of obtaining an image of a boundary within an object, said boundary representing a refractive index variation, said method comprising:*
   *irradiating said boundary with a propagated wavefront of x-rays having high lateral spatial coherence and a propagation component transverse to said refractive index variation;*
   *detecting intensity of at least a portion of said wavefront of said x-rays passing through said boundary so as to form said image, said x-rays having been refracted by said boundary such that said boundary is represented on said image by a corresponding variation in the detected intensity of said wavefront in said image, wherein the boundary and a position of detecting said intensity of at least a portion of said wavefront are separated by a distance greater than or equal to 0.3 m to enhance the contrast of said variation in the detected intensity of said wavefront; and* processing said image so as to derive from the image said corresponding variation in the detected intensity of said wavefront in said image and so identify the representation of the boundary.

41. A method as claimed in claim 40, wherein said distance is greater than or equal to 0.7 m.

42. An apparatus for obtaining an image of a boundary within an object, said boundary representing a refractive index variation, said apparatus comprising:

a source for irradiating said boundary with a propagated wavefront of x-rays having high lateral spatial coherence and a propagation component transverse to said refractive index variation;

a detector for detecting intensity of at least a portion of said wavefront of said x-rays so as to form said image, said x-rays having been refracted by said boundary such that said boundary is represented on said image by a corresponding variation in the detected intensity of said wavefront in said image;

holder means to hold an object containing said boundary and so locate the boundary at a predetermined position, whereby a separation distance between said boundary and said detector may be set to enhance the contrast of said variation in the detected intensity of said wavefront, and wherein said detector and said holder means are disposed so that said distance is greater than or equal to 0.3 m; and means for processing said image so as to derive from the image said corresponding variation in the detected intensity of said wavefront in said image and so identify the representation of the boundary.

43. An apparatus as claimed in claim 42, wherein said detector and said holder means are disposed so that said distance is greater than or equal to 0.7 m.

44. A method of obtaining an image of a boundary within an object, said boundary representing a refractive index variation, said method comprising:

irradiating said boundary with a propagated wavefront of x-rays having high lateral spatial coherence and a propagation component transverse to said refractive index variation, wherein said x-rays are generated with a source less than or equal to 20 μm in diameter;

detecting intensity of at least a portion of said wavefront of said x-rays passing through said boundary so as to form said image, said x-rays having been refracted by said boundary such that said boundary is represented on said image by a corresponding variation in the detected intensity of said wavefront in said image; and processing said image so as to derive from the image said corresponding variation in the detected intensity of said wavefront in said image and so identify the representation of the boundary.

45. A method as claimed in claim 44, wherein the boundary and a position of detecting said intensity of at least a portion of said wavefront are separated by a distance greater than or equal to 0.7 m to enhance the contrast of said variation in the detected intensity of said wavefront.

46. An apparatus for obtaining an image of a boundary within an object, said boundary representing a refractive index variation, said apparatus comprising:

a source for irradiating said boundary with a propagated wavefront of x-rays having high lateral spatial coherence and a propagation component transverse to said refractive index variation, wherein said source has a diameter less than or equal to 20 μm;

a detector for detecting intensity of at least a portion of said wavefront of said x-rays so as to form said image, said x-rays having been refracted by said boundary such that said boundary is represented on said image by a corresponding variation in the detected intensity of said wavefront in said image; and means for processing said image so as to derive from the image said corresponding variation in the detected intensity of said wavefront in said image and so identify the representation of the boundary.

47. An apparatus as claimed in claim 46, further comprising:

holder means to hold an object containing said boundary and so locate the boundary at a predetermined position, whereby a separation distance between said boundary and said detector may be set to enhance the contrast of said variation in the detected intensity of said wavefront, and wherein said detector and said holder means are disposed so that said distance is greater than or equal to 0.7 m.

* * * * *